United States Patent [19]

Benedetti et al.

[11] Patent Number: 4,472,587
[45] Date of Patent: Sep. 18, 1984

[54] PROCESS FOR OBTAINING PHTHALIC ANHYDRIDE, STARTING FROM ORTHO-XYLENE, NAPHTALENE AND THEIR MIXTURES, BY OXIDATION IN THE PRESENCE OF A SPECIFIC CATALYST AND THE CATALYST OBTAINED BY CARRYING OUT SAID PROCESS

[75] Inventors: Francesco Benedetti; Ezio Polacco; Angelo Celli, all of Milan, Italy

[73] Assignee: Carbochimica Italiana S.P.A., Milan, Italy

[21] Appl. No.: 379,396

[22] Filed: May 18, 1982

[30] Foreign Application Priority Data

Jun. 16, 1981 [IT]   Italy ................................ 22358 A/81

[51] Int. Cl.$^3$ ............................................ C07D 307/89
[52] U.S. Cl. ...................................... 549/248; 502/350
[58] Field of Search ......................................... 549/248

[56] References Cited

U.S. PATENT DOCUMENTS

| | | | |
|---|---|---|---|
| 3,799,886 | 3/1974 | Felice et al. | 252/461 |
| 3,898,249 | 8/1975 | Felice et al. | 549/248 |
| 4,077,984 | 3/1978 | Blechschmitt | 549/248 |
| 4,282,116 | 8/1981 | Reuter et al. | 549/248 |

OTHER PUBLICATIONS

Landau et al., Chemistry and Industry, Jul. 24, 1961, pp. 1143–1152.

*Primary Examiner*—Richard Raymond
*Attorney, Agent, or Firm*—Ladas & Parry

[57] ABSTRACT

The present invention concerns a process for obtaining phthalic anhydride by oxidizing ortho-xylene, naphthalene, or mixtures of the two, in the presence of a specific catalyst with a vanadium pentoxide and titanium dioxide base, and also regards the catalyst obtained by enactment of said process.

5 Claims, 9 Drawing Figures

PROCESS FOR OBTAINING PHTHALIC ANHYDRIDE, STARTING FROM ORTHO-XYLENE, NAPHTALENE AND THEIR MIXTURES, BY OXIDATION IN THE PRESENCE OF A SPECIFIC CATALYST AND THE CATALYST OBTAINED BY CARRYING OUT SAID PROCESS

The present invention concerns a process for obtaining phthalic anhydride by oxidizing ortho-xylene, naphthalene, or mixtures of the two, in the presence of a specific catalyst with a vanadium pentoxide and titanium dioxide base, and also regards the catalyst obtained by enactment of said process.

At present phthalic anhydride is obtained by two basically different procedures starting, respectively, from ortho-xylene or from naphthalene. Each of these procedures requires, for oxidation with air, a specific catalyst with a vanadium pentoxide and titanium dioxide base. These specific catalysts have a relatively brief life, and require continuous checks, changes in reaction conditions, and especially in reaction temperature, and cause the formation of pollutants which can only be tolerated in extremely low percentages. The consequence of partial deactivation of the catalyst is a drop in productivity of the production plant being used.

Reaction diagrams; compositions, and thermal balances are given as follows to better illustrate the practice of the two different procedures, respectively for oxidation with air of naphthalene, in table 1 and reaction with air of ortho-xylene in table 2, in the presence of specific catalysts with vanadium pentoxide and titanium dioxide bases, such as those presently marketed by, for example, the German Von Heyden Company.

TABLE 1

NAPHTHALENE/AIR OXIDATION REACTIONS IN THE PRESENCE OF $V_2O_5$ AND $TiO_2$ BASE CATALYSTS.

| | Composition | | Reaction values in thousands of Kcal. | |
|---|---|---|---|---|
| | % moles | % weight | Per 100 moles | Per 10 kg. |
| NAPHTHALENE → PHTHALIC ANHYDRIDE<br>(1) $C_{10}H_8 + 4\frac{1}{2}O_2 \longrightarrow C_8H_4O_3 + 2CO_2 + 2H_2O + 448$ Kcal. | 79.60 | 92.00 | 35.70 | 27.900 |
| (2) $C_{10}H_8 + 12O_2 \longrightarrow 10CO_2 + 4H_2O + 1230$ Kcal. | 12.40 | — | 12.50 | 9.750 |
| (3) $C_{10}H_8 + 7O_2 \longrightarrow 10CO + 4H_2O + 555$ Kcal.<br>($CO_2/CO$ ratio in oxidation gas approx. 2/1) | | | | |
| NAPHTHALENE → MALEIC ANHYDRIDE<br>(4) $C_{10}H_8 + 9O_2 \longrightarrow C_4H_2O_3 + 6O_2 + 3H_2O + 898$ Kcal. | 7.83 | 6.00 | 7.00 | 5.500 |
| NAPHTHALENE → 1-4 NAPHTHOQUINONE<br>(5) $C_{10}H_8 + 1\frac{1}{2}O_2 \longrightarrow C_{10}H_6O_2 + H_2O + 130$ Kcal. | 0.12 | 0.15 | 0.02 | 0.013 |

TABLE 1-continued
NAPHTHALENE/AIR OXIDATION REACTIONS IN THE PRESENCE OF $V_2O_5$ AND $TiO_2$ BASE CATALYSTS.

| | Composition | | Reaction values in thousands of Kcal. | |
|---|---|---|---|---|
| | % moles | % weight | Per 100 moles | Per 10 kg. |
| NAPHTHALENE → BENZOIC ACID (COOH) | 0.05 | 0.05 | 0.03 | 0.018 |
| (6) $C_{10}H_8 + 4\frac{1}{2}O_2 \longrightarrow C_7H_6 + 3CO_2 + H_2O + 460$ Kcal. | | | | |
| | 100.00 | — | 55.25 | 43.181 |

TABLE 2
O—XYLENE OXIDATION REACTIONS WITH AIR IN THE PRESENCE OF $V_2O_5$ AND $TiO_2$ BASE CATALYSTS.

| | Composition | | Reaction values in thousands of Kcal. | |
|---|---|---|---|---|
| | % moles | % weight | Per 100 moles | Per 10 kg. |
| O—XYLENE → PHTHALIC ANHYDRIDE | 74.20 | 102.60 | 23.002 | 21.700 |
| (1) $C_8H_{10} + 3O_2 \longrightarrow C_8H_4O_3 + 3H_2O + 310$ Kcal | | | | |
| | 17.90 | 62.70 | 16.494 | 15.560 |
| (2) $C_8H_{10} + 10\frac{1}{2}O_2 \longrightarrow 8CO_2 + 5H_2O + 1094$ Kcal | | | | |
| (3) $C_8H_{10} + 6\frac{1}{2}O_2 \longrightarrow 8CO + 5H_2O + 522$ Kcal (Ratio between $CO_2/CO$ in reaction gas approx. 3.3/1) | | | | |
| O—XYLENE → MALEIC ANHYDRIDE | 6.60 | 6.00 | 5.016 | 7.732 |
| (4) $C_8H_{10} + 7\frac{1}{2}O_2 \longrightarrow C_4H_2O_3 + 4CO_2 + 4H_2O + 760$ Kcal. | | | | |
| O—XLYENE → BENZOIC ACID (COOH) | 0.85 | 1.00 | 0.274 | 0.258 |
| (5) $C_8H_{10} + 3O_2 \longrightarrow C_7H_6O_2 + CO_2 + 2H_2O + 322$ Kcal. | | | | |

TABLE 2-continued
O—XYLENE OXIDATION REACTIONS WITH AIR IN THE PRESENCE OF $V_2O_5$ AND $TiO_2$ BASE CATALYSTS.

| | Composition | | Reaction values in thousands of Kcal. | |
|---|---|---|---|---|
| | % moles | % weight | Per 100 moles | Per 10 kg. |
| O—XYLENE → PHTHALIDE | 0.08 | 0.10 | — | — |
| (6) $C_8H_{10} + 2O_2 \longrightarrow C_8H_6O_2 + 2H_2O$ | | | | |
| O—XYLENE → CITRACONIC DIOXIDE | 0.37 | 0.40 | — | — |
| (7) $C_8H_{10} + 6O_2 \longrightarrow C_5H_4O_3 + 3CO_2 + 3H_2O$ | | | | |
| | 100.00 | — | 44.786 | 42.250 |

Note that small quantities of the following may be formed during oxidation of o-xylene: o-toluic acid, trimellitic dioxide and pyromellitic dioxide, anthraquinones, etc. To better illustrate the state of the present art, note, for example, that to produce phthalic anhydride starting from o-xylene a vanadium pentoxide and titanium dioxide base catalyst is normally used of the series F type, manufactured by the aforementioned Von Heyden Company. The guaranteed life of the type F catalyst made by Von Heyden is approximately 3 years, but, as we have already noted, the quality of the final product tends to slowly worsen during this period due to the formation of increasing quantities of by-products. Several pollutants are, in particular, formed. Production of phthalide is used as a guideline pollutant during quality-control measures. At the start this production is 0.05%, and must absolutely not exceed the limit of 0.1%. Note that in larger quantities this pollutant cannot be industrially eliminated.

The temperature must be gradually increased up to a maximum of 394° C. (pilot temperature) to keep phthalic anhydride quantities below maximum limits. At a higher temperature there would be danger of combustion, and also a decrease in output that an industry could not sustain.

Also note, in conclusion, that there would be no product improvement at constant output rates at a higher temperature. Consequently, to keep quality constant, the supply of o-xylene must gradually be reduced, with a consequent reduction in plant output and capacity. Obviously capacity can only be reduced within economic limits: beyond these limits the catalyst must be replaced, with the obvious consequences.

The present invention, to overcome these problems, proposes a mixed ortho-xylene and naphthalene feed procedure to produce phthalic anhydride using the same specific vanadium and titanium pentoxide-base catalyst, following a precise feed curve for these initial products, which integrate each other as the process proceeds in individually variable proportions going, respectively, from 100% to 0 and vice versa. The present invention also regards the vanadium pentoxide and titanium dioxide based catalysts obtained during enactment of the procedure according to the invention, usable to obtain phthalic anhydride starting from naphthalene alone or in a mixture with ortho-xylene.

The invention, finally, also regards the plant that permits enactment of the procedure, with mixed feed of ortho-xylene and naphthalene to obtain phthalic anhydride.

In particular the solution, researched and experimented by the applicant first in a pilot plant and then in an industrial plant, permits a single plant to have constant phthalic anhydride output and constant product quality, with preparation of a catalyst, a further object of the invention, which, according to prior technology, should no longer be usable because partially or completely exhausted.

The basic problem-solving idea of the present invention is that of feeding the plant with a mixture of naphthalene and orthoxylene depending on the physical-chemical conditions of the vanadium pentoxide and titanium dioxide base catalyst conditions which vary over a period of time—basically by exploiting the fact that oxidation of naphthalene requires less activation energy.

The present invention can be better understood from the following detailed description, made with special reference to the figures, which show, respectively:

FIG. 1 a diagram of outputs which can be obtained using o-xylene, naphthalene and their mixtures;

FIG. 2 a chart illustrating o-xylene and naphthalene feed possibilities in function of the months of use of the plant, and also indicating reaction temperatures and the presence of guideline-pollutants such as phthalide;

Figure 1:
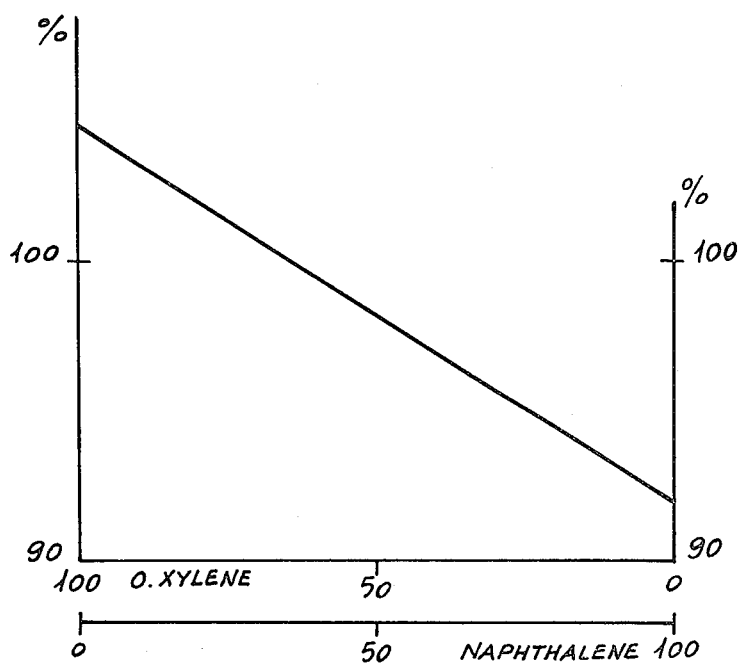

The curve in FIG. 1 clearly shows the percentage output of o-xylene, naphthalene and their mixtures, with a linear progression going from 104.5%, corresponding to 100% o-xylene feed, to 92%, corresponding to 100% naphthalene feed. The chart in FIG. 2, on the other hand, illustrates the curve of a possible mixed o-xylene and naphthalene feed, with a linear drop from the 40th month and a step-by-step drop from the 57th up to the 85th month in ortho-xylene feed, and corresponding step-by-step increase in naphthalene feed starting from the 57th month, with temperature always below 394° C.

The same chart also shows how the presence of phthalide is kept under control. The increase is practically linear up to the 61st month, and then proceeds at sawtoothed intervals, with a clear drop every time there is an increase in naphthalene feed.

It can be stated, as a guideline example only, that depending on the condition of the vanadium and titanium pentoxide based catalyst, naphthalene and ortho-xylene can be used in gradually variable proportions equal to 30/70, 50/50, 70/30, until the plant reaches 100% naphthalene. For example a production plant which, working with 1000 kg./hr. of ortho-xylene, has reached a 387° C. oxidation temperature after 40 months of operation, can then be fed with a mixture of 300 kg/hr. of naphthalene and 800 kg/hr. of ortho-xylene.

This gives an increase in feed from 1045 to 1112 kg./hr., with constant quality and stoichiometric output. For the sake of thoroughness note that there may be a slight change in the type of pollutant by-products, due to the presence of naphthoquinones, but in any case these are easily eliminated, following opportune treatment in standard raw phthalic anhydride purification plants.

Figure 3:
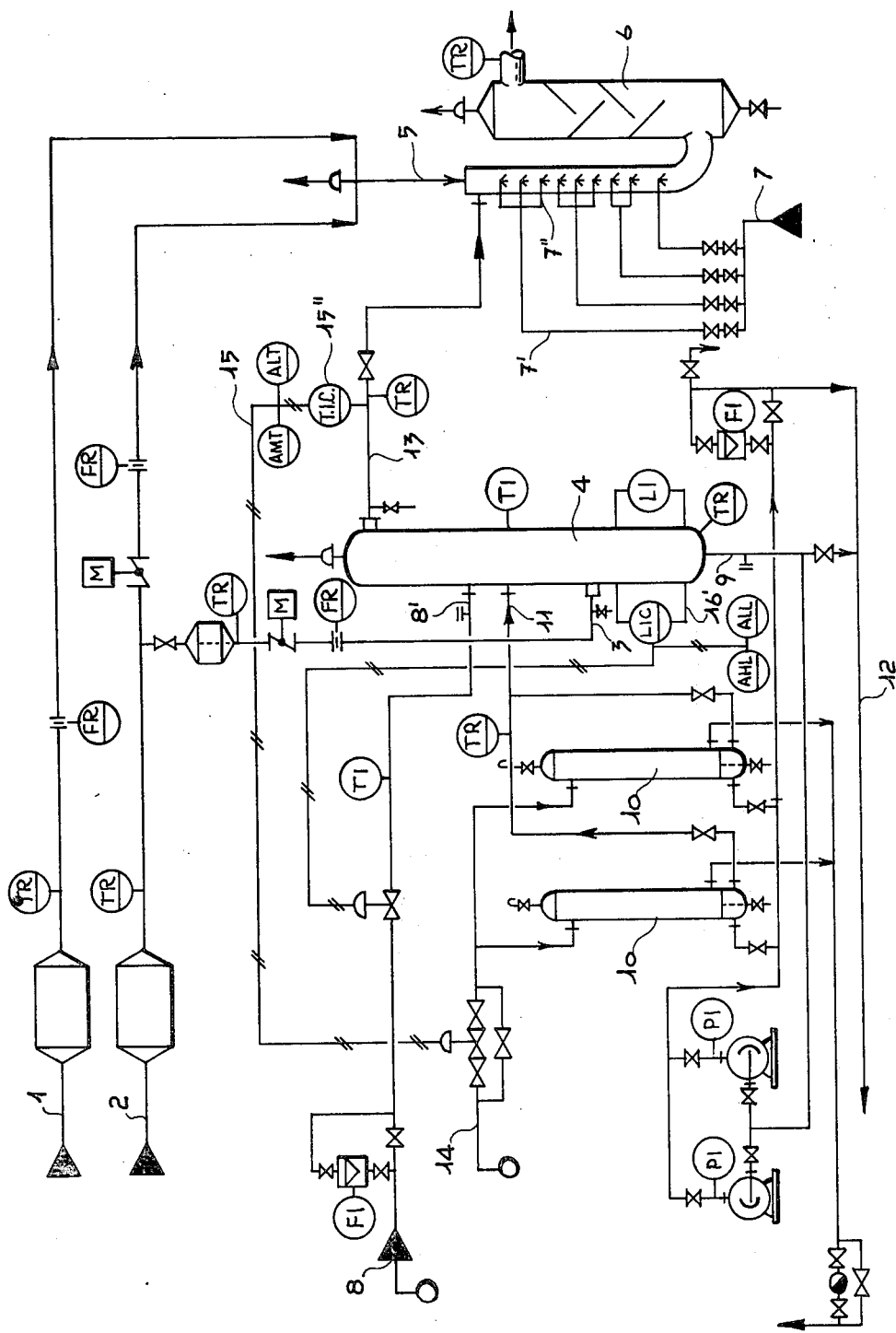
FIG. 3 shows a diagram of a possible plant for production of phthalic anhydride using the mixed feed system according to the invention.

As has been said, FIG. 3 illustrates the diagram of a possible plant for enacting the procedure according to the invention, with mixed o-xylene and naphthalene feed. This plant, for example, can be designed for a maximum naphthalene feed of 1000 kg/hr. and 2500 Nm3/hr. of air at 135° C. The air feed takes place through entry ducts 1 and 2. These feed, through duct 3, a carburetor, specified by 4, and through duct 5 another carburetor, specified by 6, for the ortho-xylene and/or the vaporized naphthalene. The ortho-xylene is fed directly from pipeline 7, which branches into several pipelines 7' and 7" feeding sprayers, whereas naphthalene is fed through high temperature pipeline 8, kept around 78° C., reaching carburetor 4 through feed pipeline 8'.

Said carburetor 4 has a discharge on the bottom 9, where naphthalene is taken and sent to a series of heat-exchangers 10 before being recycled to the carburetor through pipeline 11.

Finally, according to the invention, there is a pipeline 13 between carburetor 4 and the top part of the supply pipeline to carburetor 6. The feed to the ortho-xylene, naphthalene and their mixtures oxidation reactor starts from this last component.

A 15' temperature monitoring device is mounted on pipeline 13. This device, according to known technology, controls the delivery of vapor through feed pipeline 14.

For example vapor can be fed at a pressure of 6 kg/cm$^2$. As is evident from the above description, the plant according to the invention can vary at will its feed of o-xylene and naphthalene, and thus is free to follow a preselected feeding curve, such as the one given in FIG. 2.

One distinctive feature of the plant is that it can use the same oxidation reactor with the same catalyst, which should be exhausted according to standard technology, by opportunely integrating the feed of o-xylene with the feed of naphthalene, treated in advance in carburetor 4 before it reaches carburetor 6.

Note that, according to the invention, naphthalene can be treated in any manner, as long as it is made suitable for delivery to carburetor 6. This document does not, basically, intend to claim a single specific device that makes such delivery possible. Specifically note that the carburetor indicated as an assembly by the number 4, forms the object of another application for patent by the same applicant. As has already been said, the vanadium pentoxide and titanium dioxide based catalyst obtained by enacting the procedure according to the invention is also an object of the present invention.

To better clarify the characteristics of this catalyst, tests and microphotographs have been made, and are enclosed with the present application in tables 1, 2, 3 and 4.

Said photographs were all made under 2000 enlargements. These microphotographs show quite clearly the physical differences between the type F catalyst (tables 1 and 2) previously mentioned, and that indicated in the following by S (tables 3 and 4) according to the present invention. Porosity and surface areas have also been calculated, comparing catalyst S with marketed catalyst F.

Specifically there was an approx. 400° C. hot air pre-treatment. The sample of catalyst F was therefore subjected to calcination in air (in porcelain capsule muffle furnace) at a temperature gradually increasing to 400° C. for a total time of approximately 3 hours, with two hours at final temperature. Subsequently, prior to determination of their properties, the samples underwent degassing, by heating them to 200° C. in a 10$^{-2}$ Torr vacuum.

Calculation of total specific surface area was performed using the PET technique, by adsorption-desorption of pure nitrogen (SAPOI ppl) at the temperature of liquid nitrogen. The volume of the "dead" spaces in the sample-carrier was calculated by helium compression-expansion, again at the temperature of liquid nitrogen.

Figure 4:
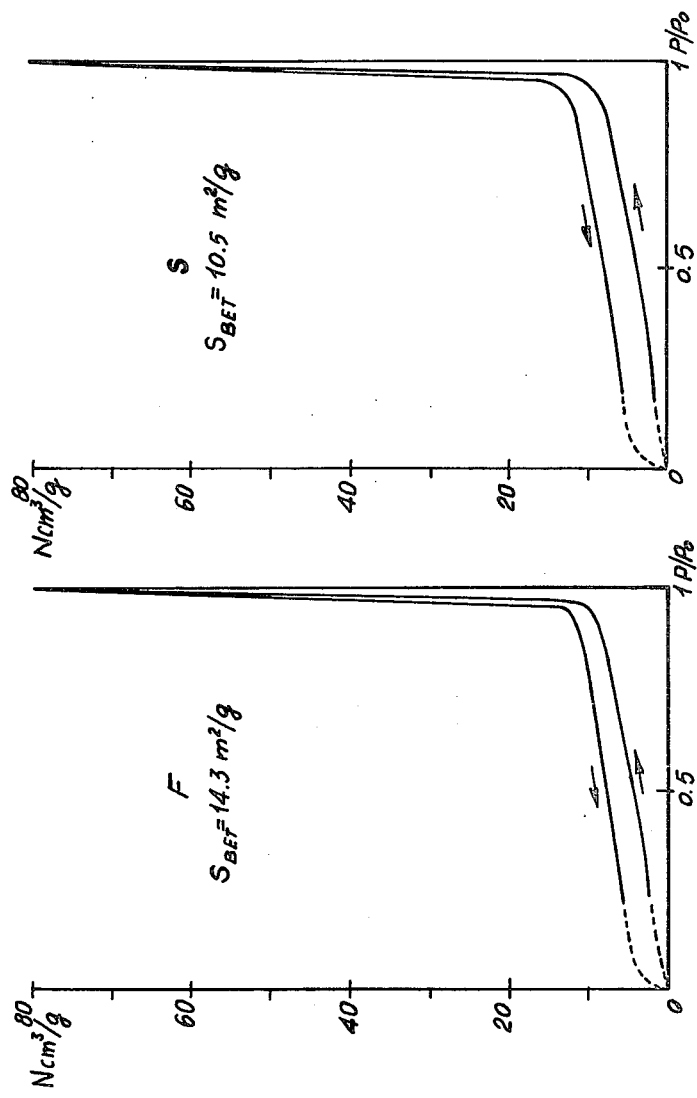
FIGS. 4 and 5 show, respectively, adsorption-desorption isothermal curves and specific volume distribution curves of the pores for samples F and S, respectively.

The data, obtained using a Sorptomatic C. Erba appliance and elaborated by a calculator using a special numerical calculation program, gave first of all the adsorption-desorption isothermal curves shown in FIG. 4 for the two samples F and S.

Total specific surface areas ($S_{BET}$) were calculated using the data for the curve segments of the isothermal adsorption-desorption chart going from 0.05 to 0.35 of relative pressure values ($P/P_o$). These areas were 14.3 and 10.5 m2/gr. for samples F and S respectively.

Figure 5:
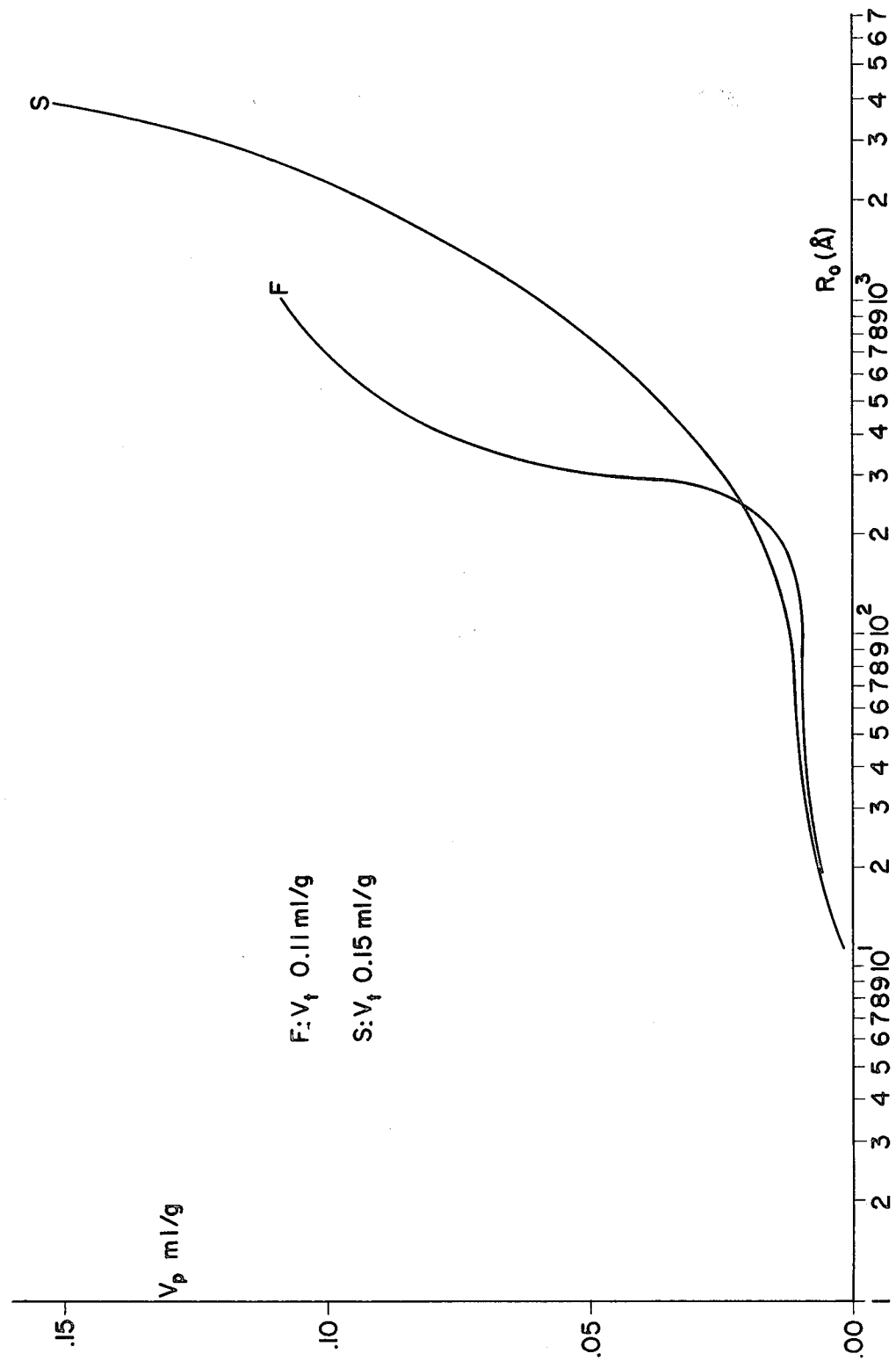
Figure 6:
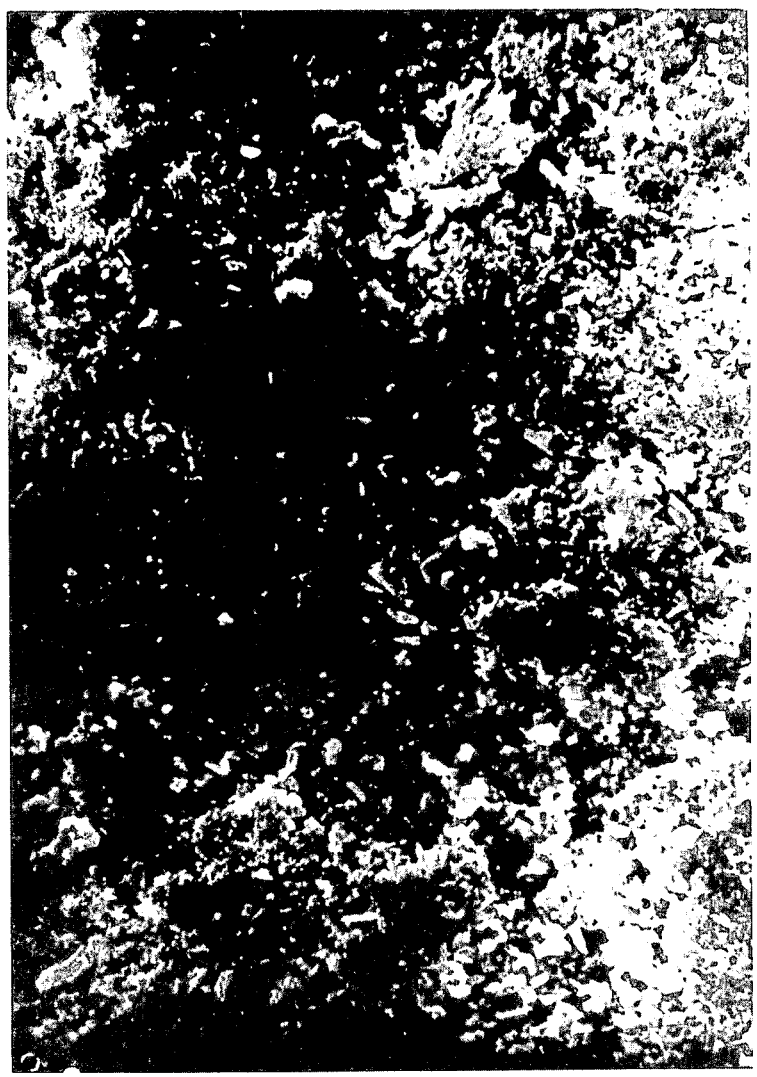
Figure 7:
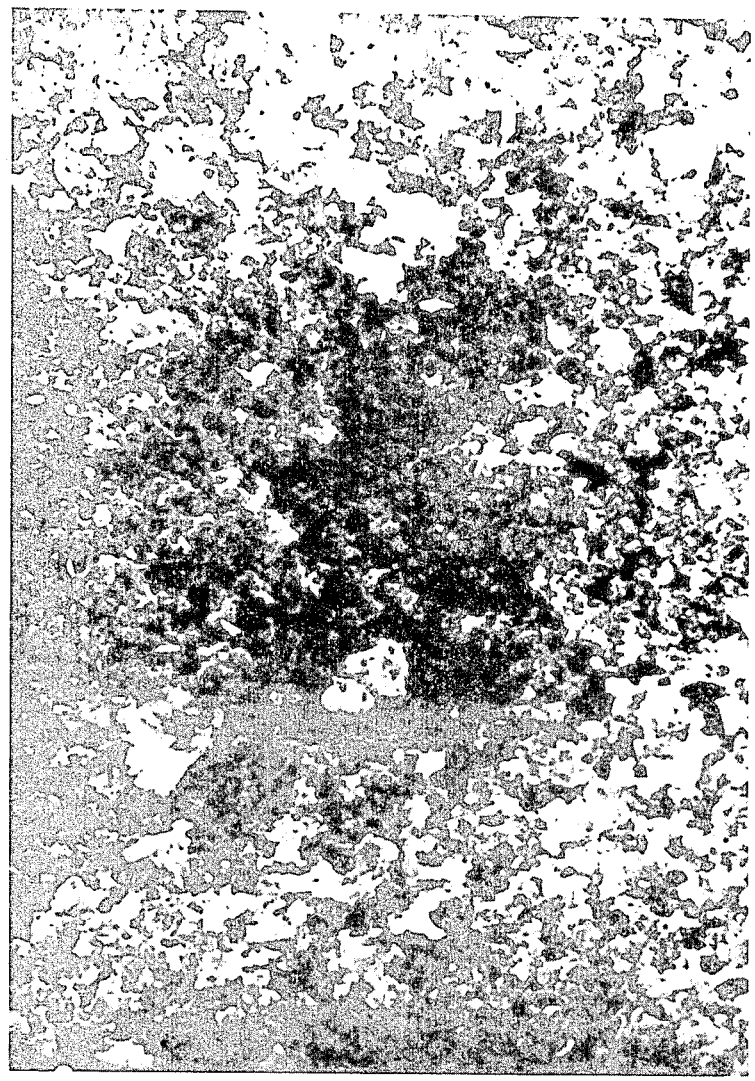
Figure 8:
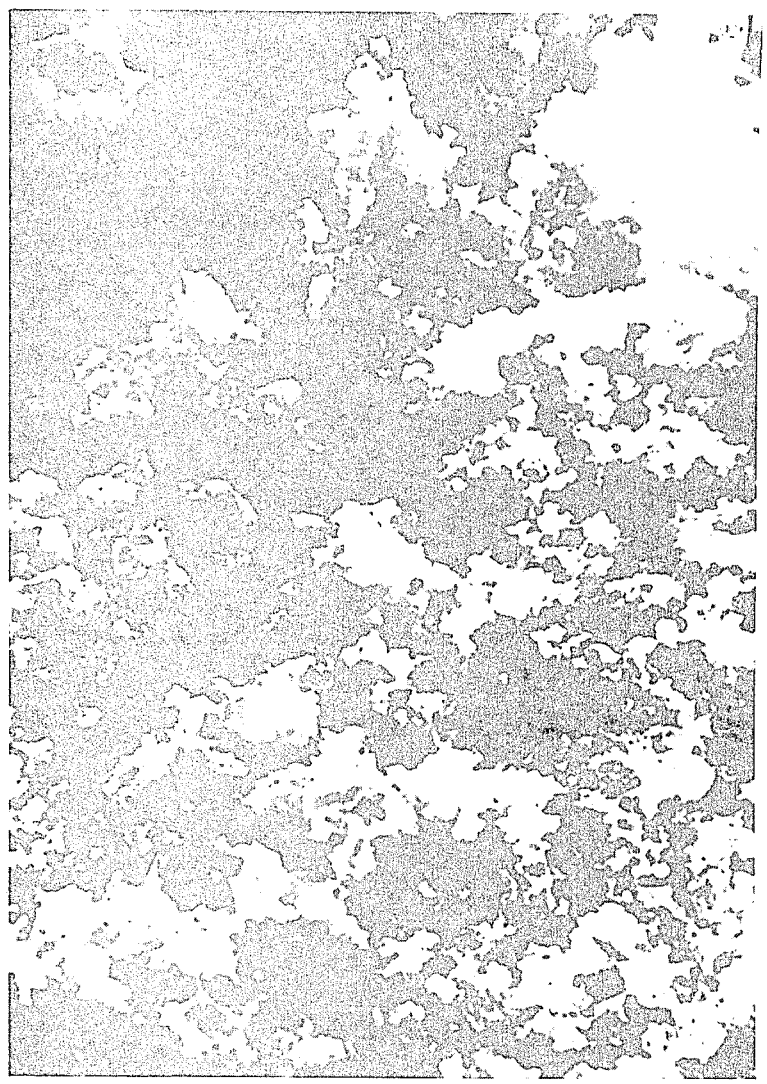
Figure 9:
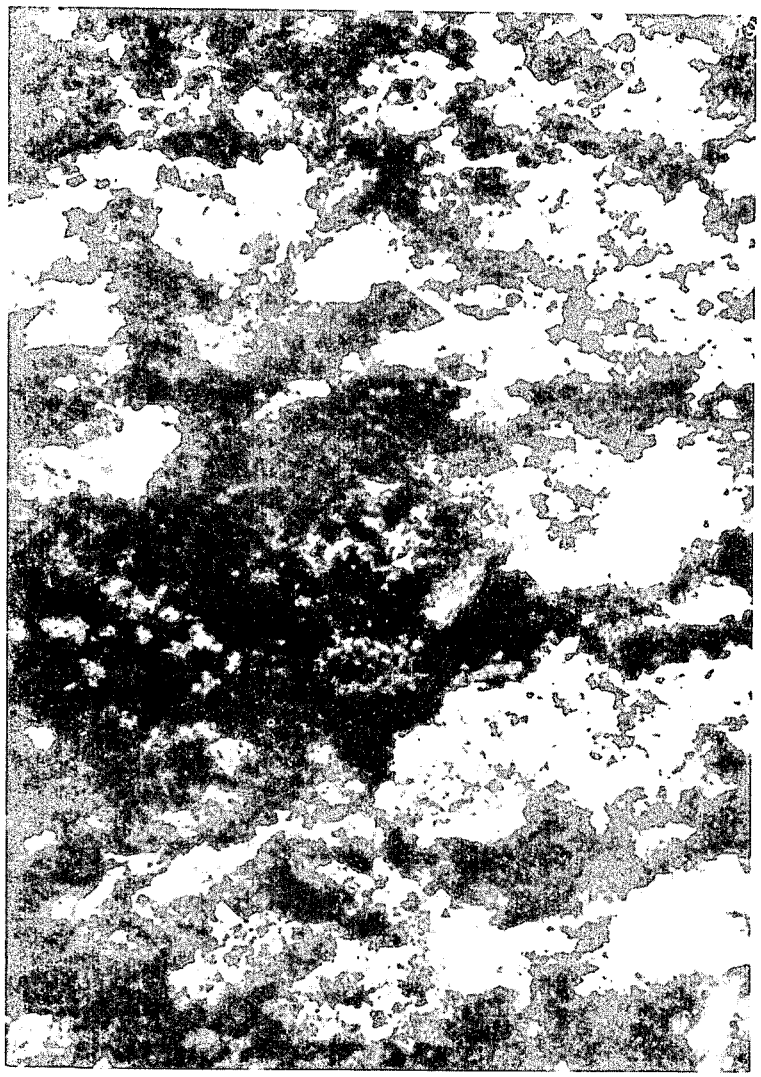

Finally, using data for the whole desorption isothermal curves, specific volume distribution curves for pores ($V_p$) were calculated in function of their radius ($R_p$), given in FIG. 5, together with the specific total volume of the pores ($V_t$), equal to 0.11 ml/gr. and 0.15 ml/gr. for samples F and S respectively.

Although only a few embodiments of the invention have been described and illustrated, now it will be easy for an expert in this field to make many modifications and variations, all of which, however, are to be held to be covered by the present invention.

We claim:

1. In an industrial process for production of phthalic anhydride in the presence of a vanadium pentoxide and titanium dioxide base catalyst, the improvement comprising employing an ortho-xylene and naphthalene mixed feed, the relative proportions of ortho-xylene and naphthalene being varied from 100% to 0% and 0% to %100, respectively, over time proportionally and in dependence upon the physical and chemical condition of the vanadium pentoxide and titanium dioxide base catalyst, said proportions of ortho-xylene and naphthalene in said feed being integrated so as to result in a monitored phthalide production below 0.1%.

Figure 2:
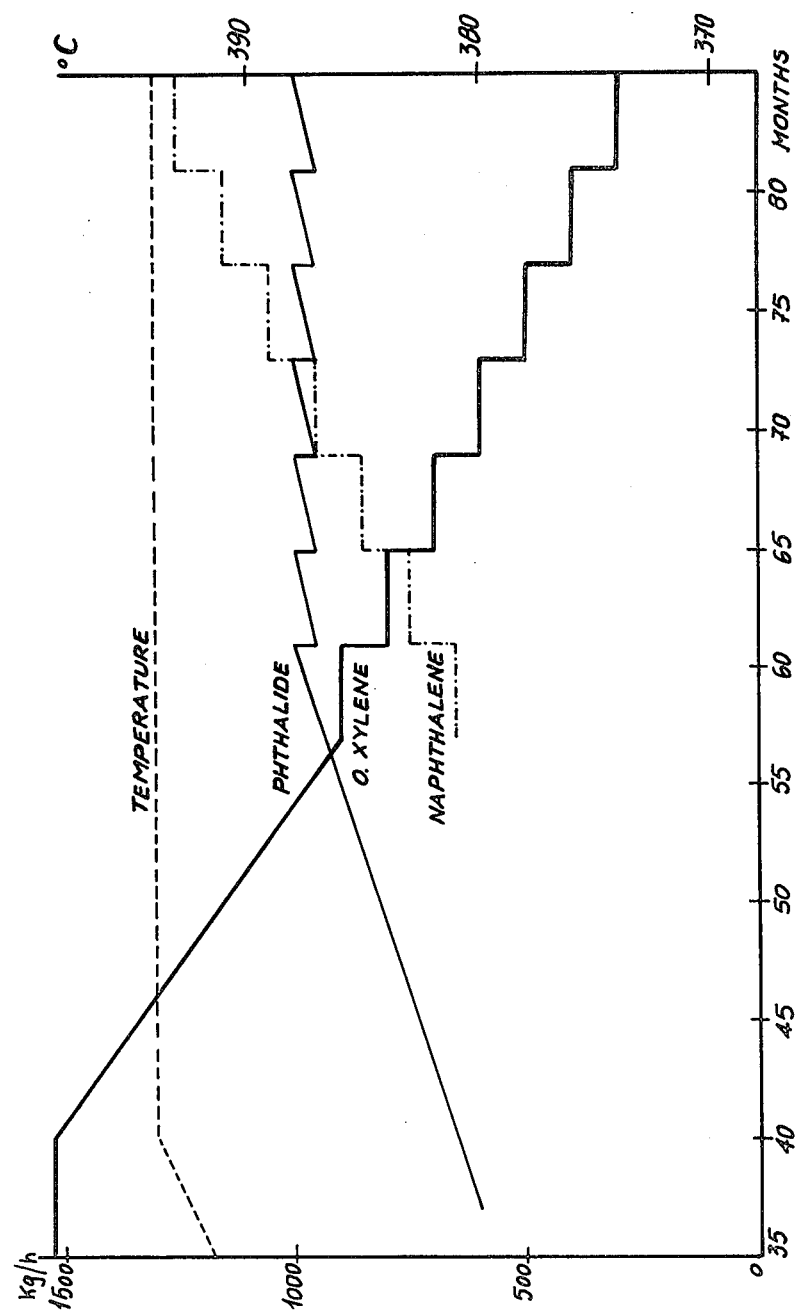

2. A process as defined in claim 1, wherein said feed is adjusted in amount and relative proportions of ortho-xylene and naphthalene substantially in accordance with the integrative feed chart as illustrated in FIG. 2.

3. A process as defined in claim 1, wherein naphthalene is first introduced into said feed after about the 50th month of operation.

4. A process as defined in claim 1, wherein naphthalene is evaporated and mixed with air before introduction into an oxidation reactor.

5. A process as defined in claim 1, wherein naphthalene is evaporated in a carburetor into which said naphthalene is fed at a temperature between 70° and 85° C., said carburetor having a discharge at the bottom thereof wherefrom naphthalene is removed and sent to a series of heat-exchangers before being recycled to said carburetor.

* * * * *